United States Patent [19]
Flax

[11] Patent Number: 4,475,400
[45] Date of Patent: Oct. 9, 1984

[54] METHOD AND MEANS FOR IMPROVING IMAGE IN AN ULTRASONIC SCANNING SYSTEM

[75] Inventor: Stephen W. Flax, Waukesha, Wis.

[73] Assignee: General Electric Company, Rancho Cordova, Calif.

[21] Appl. No.: 398,818

[22] Filed: Jul. 16, 1982

[51] Int. Cl.³ .............................................. G01N 29/04
[52] U.S. Cl. .................................................. 73/631
[58] Field of Search ............. 73/1 DV, 631, 599, 627, 73/620, 602, 618; 128/660

[56] References Cited

U.S. PATENT DOCUMENTS

| | | | |
|---|---|---|---|
| 3,309,914 | 3/1967 | Weighart | 73/631 |
| 4,016,750 | 4/1977 | Green | 73/631 |
| 4,172,386 | 10/1979 | Cribbs et al. | 73/618 |
| 4,204,433 | 5/1980 | Cribbs et al. | 73/620 |
| 4,361,043 | 11/1982 | Engle | 128/660 |

*Primary Examiner*—Anthony V. Ciarlante
*Attorney, Agent, or Firm*—Flehr, Hohbach, Test, Albritton & Herbert

[57] ABSTRACT

The image display in an ultrasonic scanning system is improved by compensating electrical signals representing reflections of ultrasonic waves at various distances from a transducer in accordance with the gain and sensitivity of the transducer to reflections at the various distances from the transducer. Gain represents a first order adjustment and sensitivity to change represents a second order adjustment.

8 Claims, 3 Drawing Figures

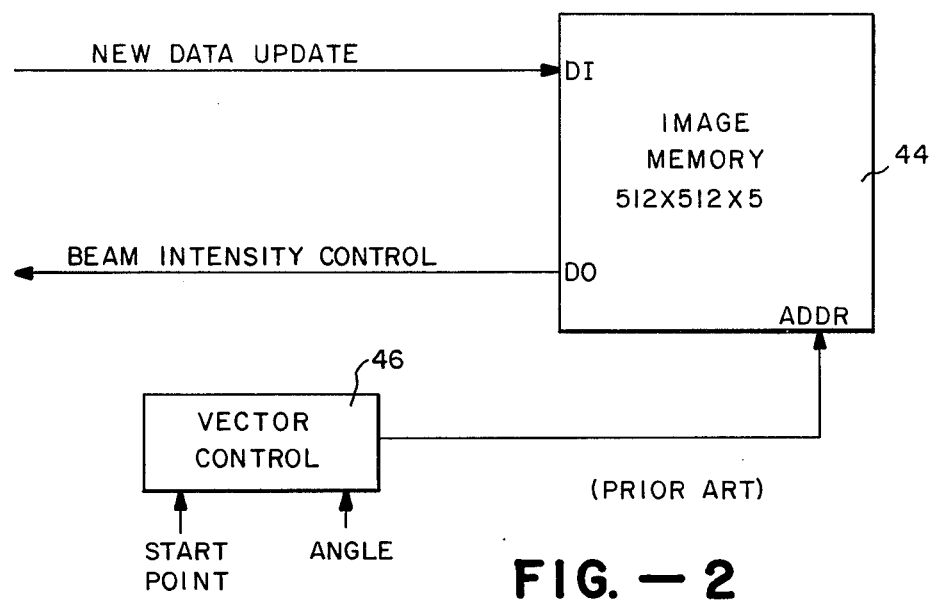
FIG. — 2 (PRIOR ART)
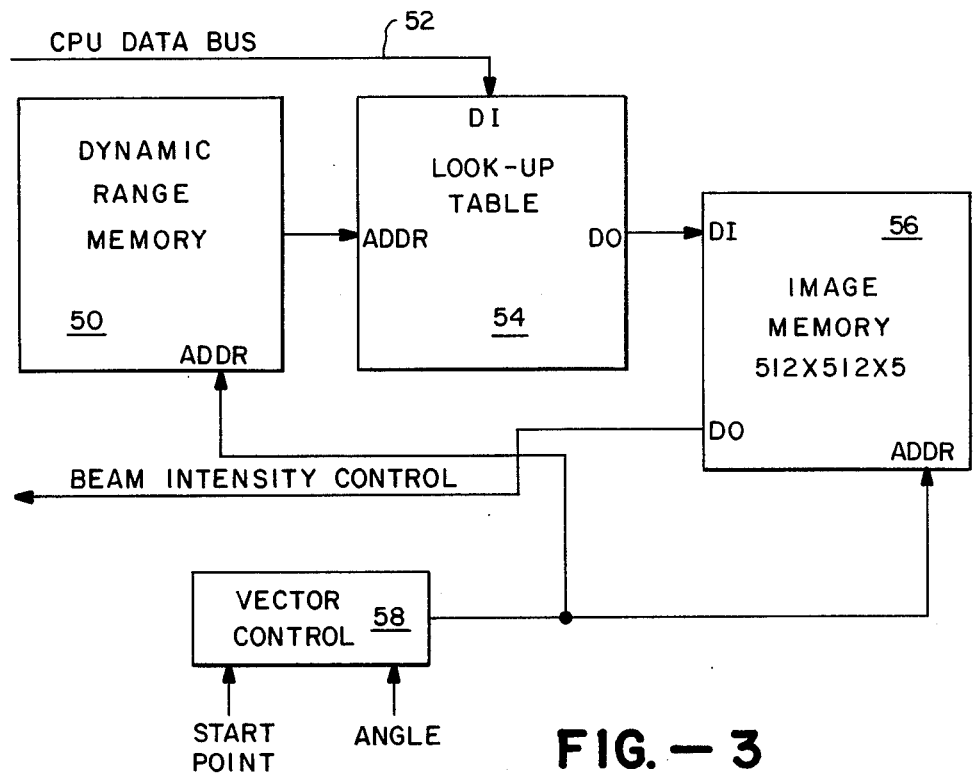
FIG. — 3

METHOD AND MEANS FOR IMPROVING IMAGE IN AN ULTRASONIC SCANNING SYSTEM

This invention relates generally to ultrasonic scanning systems such as used for medical diagnostic purposes, and more particularly the invention relates to a method and means for improving the display image in such a system.

Ultrasonic diagnostic systems are known and commercially available for diagnostic purposes. See for example U.S. Pat. N0. 4,172,386 for "Video A Trace Display System for Ultrasonic Diagnostic System" and U.S. Pat. No. 4,204,433 for "Computerized Ultrasonic Scanner With Technique Select". The commercially available Datason ultrasound system of General Electric Company provides both real time and static images on a television display.

Briefly, such systems utilize sound transducers to transmit ultrasonic (e.g. on the order of several megahertz) waves into a patient and to receive echo signals. The transducer is attached to a plurality of hinged arms for movement in a single plane, and potentiometers associated with the hinged arms produce signals which identify the transducer position. The echo signals are applied to a time gain compensated amplifier to adjust the echo signals for attenuation in passing through the patient. The adjusted signals are then passed through an analog to digital conversion and video processing circuitry and thence to scan converter circuitry for display formatting. The display comprises a plurality of pixels in horizontal rows and vertical columns with each pixel having a brightness level in response to the input signal. Conventionally, the brightness is defined by a 32 level Gray-scale, hence the pixel brightness level requires a 5 bit digital code. The pixel brightness codes are stored in a random access memory with the memory periodically updated in response to video signals produced from the ultrasonic scanner.

A recognized problem in such system in the non-uniform beam profile of focused transducers. Scan images appear to be brighter and more sensitive in the region of focus of the transducer than in the regions before and after the region of focus. The increased sensitivity of transducers to energy in the focal region can result in aesthetically displeasing image displays due to the Gray-scale variations.

Gain compensation is used to compensate for the brightness variation resulting from the increased sensitivity of the transducer to energy in the region of focus. For example, U.S. Pat. No. 4,356,731 for "Method and Means for Generating Time Gain Compensation Control Signal for Use in Ultrasonic Scanner and the Like" discloses an ultrasonic scanner which can digitally adjust the time gain control signal of the TGC amplifier and thereby vary the gain to achieve a relatively uniform brightness in the display.

However, adjusting the time gain control signal compensates only for the first order (e.g. gain) variations in the transducer. In accordance with the present invention compensation for second order variations is provided to thereby improve texture of a displayed image.

In carrying out the invention in accordance with a preferred embodiment, a uniform phantom is scanned and the textural variance is measured as a function of depth. The measured data is then used to generate a lookup table which alters dynamic range of the transducer with depth. The lookup table is used with data from the scanning system to address a memory of mapped values for beam intensity in the display. Accordingly, a smoother display which is more aesthetically pleasing is realized.

Thus, an object of the invention is an ultrasonic scanning system having improved image display.

Another object of the invention is a method of limiting dynamic range of a transducer with depth to thereby provide data for a smoother display image.

The invention and objects and features thereof will be more readily apparent from the following detailed description and appended claims when taken with the drawing, in which:

FIG. 2 is a functional block diagram of the image memory portion of the system of FIG. 1.

FIG. 3 is a functional block diagram of an image memory with dynamic range compensation in accordance with one embodiment of the present invention.

Figure 1:
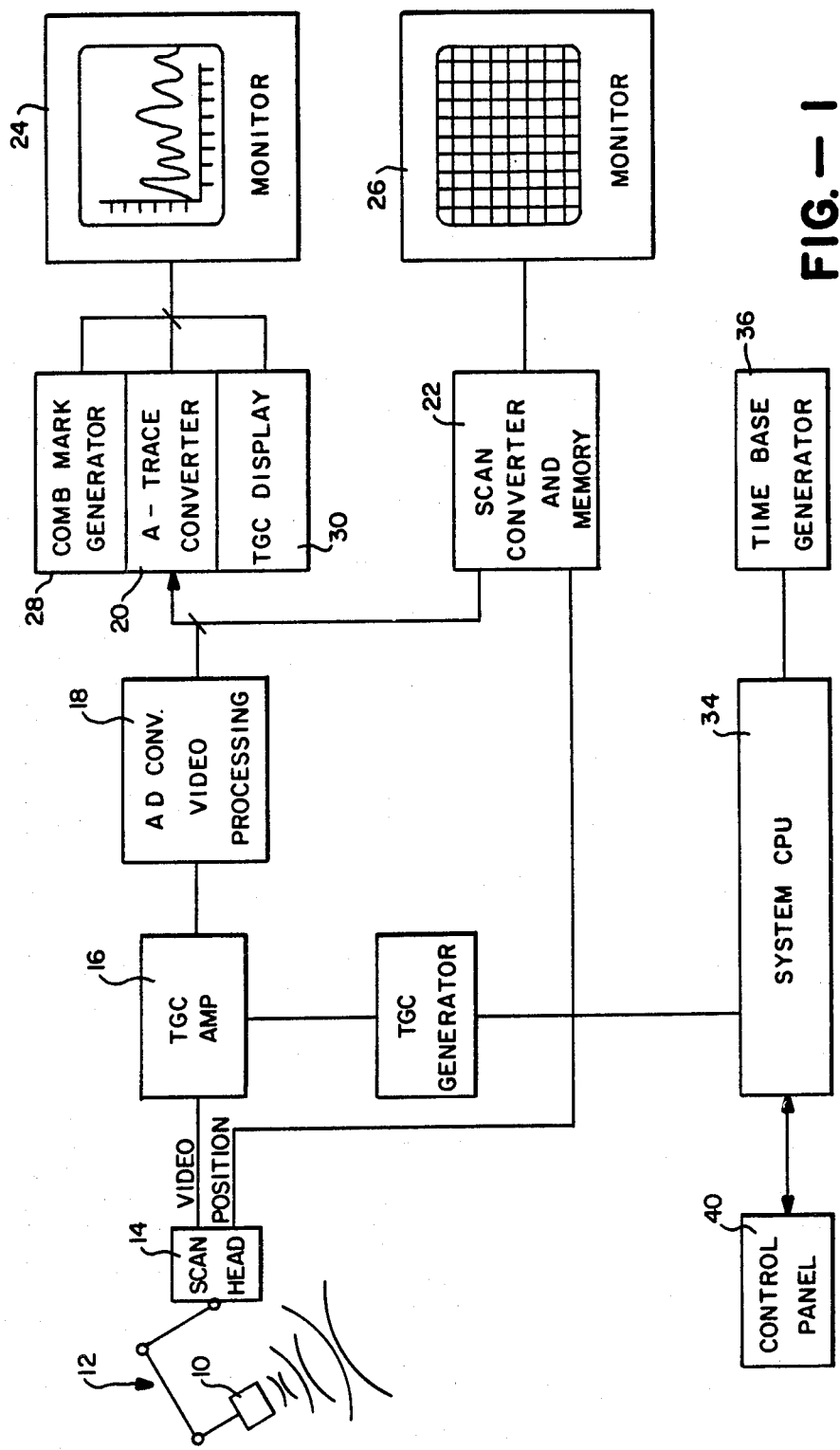
FIG. 1 is a functional block diagram of an ULTRASONIC scanner system.

Referring now to the drawings, FIG. 1 is a functional block diagram of an ultrasonic scanner. The system includes transducer 10 mounted on a hinged arm system shown generally at 12 whereby transducer 10 can move freely in a single plane. Potentiometers in scan head 14 and associated with the arms of the system generate start point and angle signals indicative of the X and Y position of the scanner 10 in the plane of motion.

Scanner 10 transmits ultrasonic signals (e.g. on the order of 5 megahertz) and generates electrical signals in response to reflections of transmitted ultrasonic signals. The generated signals are attenuated in time due to attenuation of the ultrasonic signal passing through a patient.

The attenuated video signal is then applied to time gain compensated amplifier 16, and the amplified signal is then applied to analog to digital conversion and video processing circuitry 18. The output of circuitry 18 is then applied to A trace converter circuitry 20 and to scan converter and memory circuitry 22 which generate the signals for controlling television monitors 24 and 26, respectively.

The A trace converter generates a signal for real time display of the amplitude of each reflected ultrasonic wave. The A trace data applied to monitor 25 identifies a horizontal position on the monitor (e.g. 512 positions) and an amplitude or vertical position associated with each X position. This data controls the intensity of the electron beam in the display during raster scanning of the beam. Scale markings for the displayed A trace are generated by comb mark generator 28, and a time gain compensation curve is provided by generator 30.

A section view of the patient is displayed on monitor 26 in response to the scan converter and memory 22. The signal from circuitry 18 is converted for storage in a 512 by 512 memory matrix with each point of the matrix accommodating a 5 bit brightness code. The matrix corresponds to the pixels on the display of monitor 26 with the brightness code being indicative of the Gray-scale for the pixels.

System control is provided by central processing unit 34 which also drives the time base generator 36 which generates the timing signals for the system. A time gain compensation (TGC) control generator 38 generates the control signal for amplifier 16 and a control panel 40 is provided for manual control of the system for the central processing unit.

FIG. 2 is a functional block diagram of the image memory portion of the scan converter and memory 22 of FIG. 1. As above indicated, the image memory 44 is a random access memory having storage locations corresponding to the pixels of the display of monitor 26. In the Datason system for example, the display comprises an array of pixels corresponding to 521 X positions and 512 Y positions, and the signal intensity for each pixel is defined by 5 bit code. Consequently, memory 44 has 512 X addresses. 512 Y addresses, with each X and Y location accommodating 5 bits of data.

As an ultrasonic beam is transmitted through a patient, a vector generator 46 in the scan converter 22 receives the start point and angle of the ultrasonic transducer and therefrom generates a vector including a plurality of addressable pixels. These pixel addresses are used to address and update memory 44 with the data at the address readout for beam intensity control in the monitor. As data for a pixel is read out of memory 44, the new data can be provided to the memory to update the pixel.

Focused transducers generate a non-uniform beam profile, and scan images appear to be brighter and more sensitive in the region of focus than before or after the region. The time gain control amplifier compensates for these variations. However, sensitivity to intensity variation, a second order effect, can still distort the image. The present invention provides second order compensation.

FIG. 3 is a functional block diagram of an image memory with dynamic range compensation in accordance with one embodiment of the invention. A dynamic range memory 50 stores values of transducer dynamic range with depth. Output from the dynamic range memory is used in conjunction with incoming data on the CPU bus 52 to address a lookup table 54. Table 54 provides image control data based on the data and the dynamic range corresponding to the depth at which the data was obtained. Thus, data on the bus is adjusted in accordance with the dynamic range compensation with the compensated data then applied to the image memory 56. The beam intensity control signal is obtained from the image memory 56 as in FIG. 2.

As data from a vector is applied on the bus 52, vector control 58 addresses the dynamic range memory 50 to provide for the dynamic range compensation in accordance with depth of the vector. Vector control 58 also controls the addressing of image memory 56, as in FIG. 2.

Data for the dynamic range memory 50 is obtained by scanning a uniform phantom (after the beam profile is compensated by a time gain control signal so that the mean brightness is uniform) and the textural variance is measured as a function of the depth. Data for the dynamic range memory 50 is then generated based on the necessary compensation to provide a uniform image display of the phantom. Accordingly, when the system is scanning real anatomy changes in intensity or texture variances will be more related to the tissue than to the characteristics of the imaging system. The resulting display image is aesthetically more pleasing than in a conventional system without dynamic range compensation.

While the invention has been described with reference to a specific embodiment, the description is illustrative of the invention and is not to be constructed as limiting the invention. Various modifications and applications may occur to those skilled in the art without departing from the true spirit and scope of the invention as defined by the appended claims.

What is claimed is:

1. An ultrasonic scanning system comprising
   transducer means for directing an ultrasonic beam into a body and generating electrical signals in response to reflections of said ultrasonic beam from said body,
   amplifier means for amplifying said electrical signals in accordance with a time gain control signal,
   analog to digital conversion means operably connected with said amplifier means for converting the amplified electrical signals to digital form,
   a dynamic range memory for storing transducer dynamic range compensation values for said amplified electrical signals in accordance with depth in said body of said reflections,
   a look-up table of beam intensity control values, said look-up table having address means interconnected to receive values from said dynamic range memory and the digital form of the amplified electrical signals,
   an image memory for storing beam intensity values,
   means connecting the output of said look-up table to the input of said image memory,
   vector control means for addressing said image memory, and
   a video display operably connected to receive beam intensity control signals from said image memory.

2. In an ultrasonic scanning system in which electronic signals are generated nonuniformly as a function of reflection depth by a transducer in response to said transducer receiving reflected ultrasonic signals, means for compensating said electronic signals comprising,
   a dynamic range memory for storing values of dynamic range of the transducer in response to signals reflected from various depths away from the transducer,
   an addressable look-up table of beam intensity values, and
   means for providing values of said electronic signals and data from said dynamic range memory as addresses to said look-up table for obtaining compensated values of said electronic signals.

3. Means for compensating as defined by claim 2 wherein said electronic signals are digital data representing amplified electrical signals generated by the transducer.

4. Means for compensating as defined by claim 3 and further including an image memory operably connected to said look-up table to receive and store beam intensity values.

5. Means for compensating as defined by claim 4 and further including vector control means for addressing said dynamic range memory and said image memory in accordance with distance from the transducer of a vector position for which said digital data represents.

6. In an ultrasonic scanning system, a method of improving an image display comprising the steps of
   determining measures of dynamic range of a transducer for various distances from the transducer,
   storing said measures in a first memory in accordance with distances from the transducer,
   storing values of beam control data in a second memory in accordance with said measures of dynamic range, addressing said second memory with beam intensity values and said measures to obtain compensated beam intensity control signals, and applying said compensated beam intensity control signals to a video display.

7. The method as defined in claim 6 and further including the step of addressing said first memory in accordance with distances from the transducer which are represented by the beam intensity values applied as addresses to said second memory.

8. A method of improving an image display in an ultrasonic scanning system having transducer means for transmitting ultrasonic signals and generating electrical signals in response to ultrasonic signals reflected from various distances from the transducer, said method comprising the step of compensating said electrical signals in accordance with the dynamic range of said transducer in responding to reflections from said various distances.

* * * * *

UNITED STATES PATENT AND TRADEMARK OFFICE
CERTIFICATE OF CORRECTION

PATENT NO. : 4,475,400
DATED : October 9, 1984
INVENTOR(S) : Stephen W. Flax

It is certified that error appears in the above—identified patent and that said Letters Patent is hereby corrected as shown below:

Col. 1, line 40, "in" (second occurrence) should be --is--.

Col. 2, lines 14 and 15, "ULTRA-SONIC" should be --ultrasound--.

Col. 3, line 7, "521" should be --512--.

Col. 3, line 66, "constructed" should be --construed--.

Signed and Sealed this

Second Day of July 1985

[SEAL]

*Attest:*

DONALD J. QUIGG

*Attesting Officer*  *Acting Commissioner of Patents and Trademarks*